United States Patent [19]

Vukos et al.

[11] Patent Number: 5,484,429
[45] Date of Patent: Jan. 16, 1996

[54] INTERLABIAL SANITARY PAD

[75] Inventors: John P. Vukos; Randy E. Meirowitz, both of Neenah, Wis.

[73] Assignee: Kimberly-Clark Corporation, Neenan, Wis.

[21] Appl. No.: 101,523

[22] Filed: Aug. 3, 1993

Related U.S. Application Data

[63] Continuation of Ser. No. 976,152, Nov. 13, 1992, abandoned.

[51] Int. Cl.⁶ .................................................. A61F 13/15
[52] U.S. Cl. ........................ 604/385.1; 604/378; 604/387
[58] Field of Search ................................. 604/358, 378, 604/385.1, 387

[56] References Cited

U.S. PATENT DOCUMENTS

| | | | |
|---|---|---|---|
| 3,726,277 | 4/1973 | Hirschman | 128/285 |
| 3,805,790 | 4/1974 | Kaczmarzyk et al. | 604/385.1 |
| 3,983,873 | 10/1976 | Hirschman | 128/285 |
| 4,095,542 | 6/1978 | Hirschman | 112/262 |
| 4,142,476 | 3/1979 | Hirschman | 112/262 |
| 4,175,561 | 11/1979 | Hirschman | 128/296 |
| 4,196,562 | 4/1980 | Hirschman | 53/450 |
| 4,360,022 | 11/1982 | Usami et al. | 128/290 R |
| 4,595,392 | 6/1986 | Johnson et al. | 604/385 A |
| 4,623,341 | 11/1986 | Roeder | 604/385 |
| 4,631,062 | 12/1986 | Lassen et al. | 604/385 R |
| 4,673,403 | 6/1987 | Lassen et al. | 604/385 R |
| 4,699,619 | 10/1987 | Bernardin | 604/378 |
| 4,743,245 | 5/1988 | Lassen et al. | 604/385 R |
| 4,778,459 | 10/1988 | Fuisz | 604/378 |
| 4,804,380 | 2/1989 | Lassen et al. | 604/385.1 |
| 4,820,295 | 4/1989 | Chapas et al. | 604/385.1 |
| 4,846,813 | 7/1989 | Raley | 604/385.1 |
| 4,846,824 | 7/1989 | Lassen et al. | 604/385.1 |
| 4,886,697 | 12/1989 | Perdelwitz, Jr. et al. | 428/192 |
| 4,931,357 | 6/1990 | Marshall et al. | 428/284 |
| 4,950,262 | 8/1990 | Takagi | 604/378 |
| 5,009,653 | 4/1991 | Osborn, III | 604/385.1 |
| 5,383,868 | 1/1995 | Hyun | 604/385.1 |

FOREIGN PATENT DOCUMENTS

| | | | |
|---|---|---|---|
| 0139351 | 5/1985 | European Pat. Off. | 5/44 |
| 0157649 | 10/1985 | European Pat. Off. | 15/2 |
| 61-28003 | 2/1986 | Japan | 604/385.1 |
| 410702 | 5/1934 | United Kingdom | 604/385.1 |
| 754481 | 8/1956 | United Kingdom | 81/02 |
| 1543915 | 4/1979 | United Kingdom . | |
| 2233235 | 1/1991 | United Kingdom | 13/15 |
| 90/04956 | 5/1990 | WIPO | 13/16 |
| 9012130 | 10/1990 | WIPO | D01D 5/253 |

*Primary Examiner*—Randall L. Green
*Assistant Examiner*—Rob Clarke
*Attorney, Agent, or Firm*—Mark L. Davis

[57] ABSTRACT

An interlabial sanitary pad is disclosed including a pickup module containing an absorbent which is adapted to fit in or adjacent to a vaginal opening, a capacity module containing an absorbent which is adapted to be positioned remote from the vaginal opening, and fluid-wicking fibers serving as the absorbent and further communicating with both the pickup and capacity modules for carrying fluid from the pickup module to the capacity module. The fluid-wicking fibers are longitudinally oriented and packed in the capacity module at a bulk density greater than in the pickup module. The pickup module has a fluid-pervious cover, while the capacity module has a fluid-impervious baffle capable of containing fluid therein. The capacity module can have a flattened fan shape and can contain superabsorbent.

16 Claims, 1 Drawing Sheet

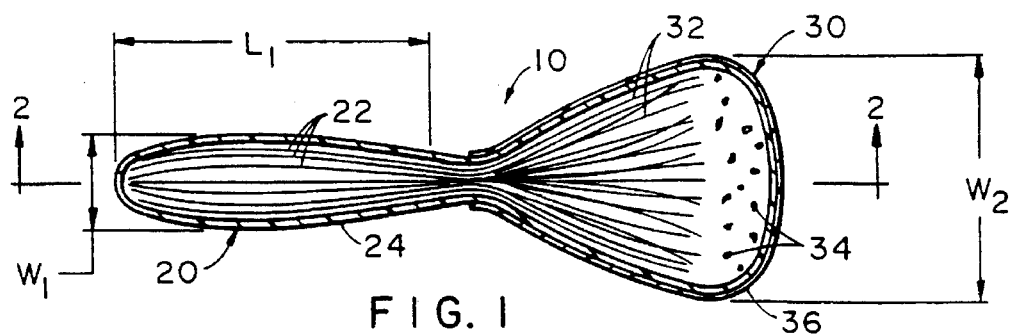
FIG. 1
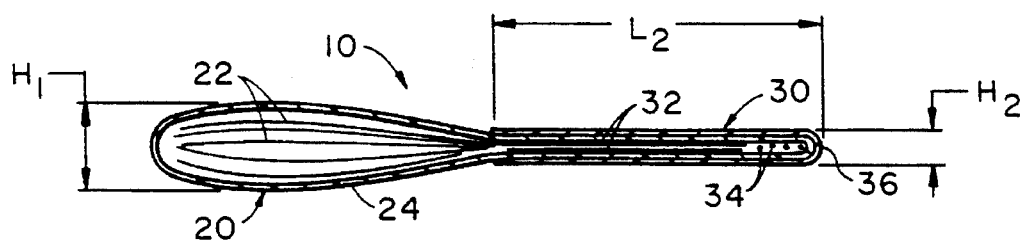
FIG. 2
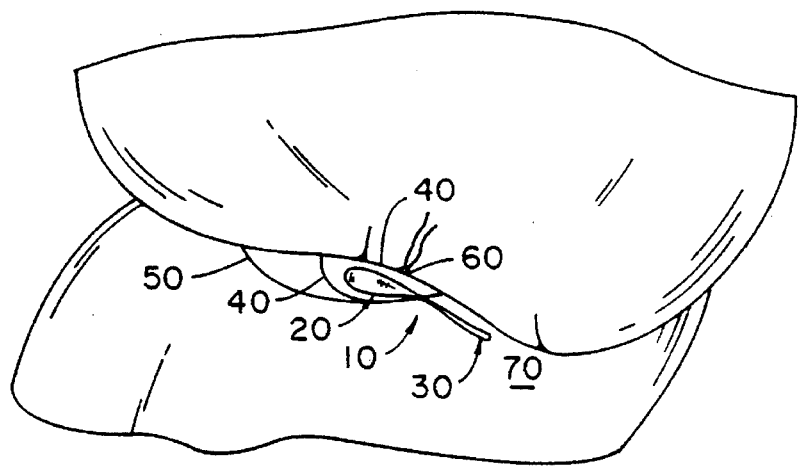
FIG. 3
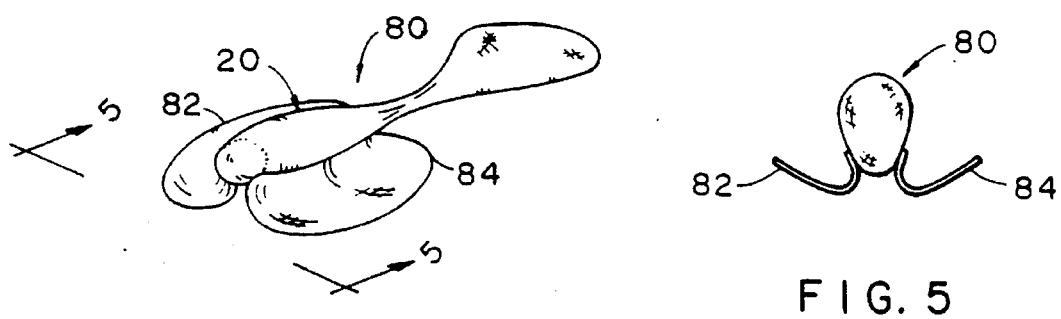
FIG. 4
FIG. 5

INTERLABIAL SANITARY PAD

This is a continuation of U.S. patent application 07/976,152 filed Nov. 13, 1992, now abandoned.

FIELD OF THE INVENTION

This invention relates generally to the field of feminine sanitary protection devices to absorb and/or contain menstrual fluids and other body exudates. More specifically, this invention relates to an interlabial pad which provides comfort and discretion in appearance.

BACKGROUND OF THE INVENTION

Conventional feminine sanitary protection devices designed to absorb body fluid, including menses, come in functional designs which can be grouped into four categories. In the first category, sanitary napkins are worn externally about the pudendal area and are designed primarily for heavy flow. Second, panty liners are thin products developed for light flow. Third, tampons are designed to be positioned internally within the vagina. Last, interlabial pads are designed to reside at least partially within the wearer's labia minora.

In the first category, sanitary napkins can have high absorptive capacity with either a thin or thick absorptive element. However, compressive forces of the wearer's thighs and pudendal region during any physical movement, such as walking, can cause the sanitary napkin to shift from its original position protecting the vulvar area. After a relatively short period of time, the sanitary napkin may move away from the vaginal orifice. The wearer's movement, particularly vigorous movement such as rapid walking or running, can also cause discomfort, such as by rubbing or chafing in the sensitive vulvar area.

In addition to concerns of sanitary napkin movement and wearer discomfort, a concern of high degree of wearing awareness is present. Some thick sanitary napkins have a high profile appearance when viewed through a wearer's outer garments. The sanitary napkins can be very apparent when worn with tight-fitting clothing, including slacks, body suits, swim suits, or similarly thin or close-fitting outer garments.

In the second category, panty liners have been developed for light or low menstrual flows. Some panty liners have the same problems associated with sanitary napkins, although their thin profile makes them more flexible, less obtrusive in appearance, and generally more comfortable than the bulky sanitary napkins. However, the thin-profile panty liners can be a drawback in the performance area of absorptive capacity.

Tampons, as a third category of feminine care devices, are worn internally within the vaginal canal to intercept body fluid. Some women, from a personal standpoint, find wearing tampons to be physically or psychologically disagreeable. Furthermore, some tampons may not function correctly to prevent leakage, because radial expansion of the tampon within the vaginal canal does not form a perfect seal. Yet, without such radial expansion and swelling of the tampon within the vaginal canal, the tampon fails to serve as a reliable sanitary protection device.

Interlabial pads, as a fourth category of feminine care devices, can be viewed as a hybrid between sanitary napkins and tampons. Interlabial pads provide a prominence or projection designed to be disposed within a woman's labia minora. Interlabial pads can provide a preferred profile of appearance when viewed through a wearer's outer garments and do not have the same problems of reliance on swelling within the vaginal canal as required by tampons. However, currently available interlabial pads have only limited capacities for the amount of body fluid which can be absorbed before creating wearer discomfort or failure by leaking through a wearer's outer garments.

U.S. Pat. Nos. 3,726,277, 3,983,873, and 4,175,561, issued to Hirschman, disclose interlabial hygienic pads which are commercially sold as the Fresh 'n Fit padette. These pads are designed to be positioned between the labia minora, and they have only a low capacity for containing body fluid because of the small amount of absorbent which can comfortably fit between the labia minora.

Now, an interlabial pad has been developed which is comfortable to wear while providing adequate protection.

SUMMARY OF THE INVENTION

Briefly, this invention relates to an interlabial sanitary pad for absorbing and containing menstrual fluids. The interlabial sanitary pad has a fluid pickup module adapted to fit into the labia minora area of a female, a capacity module containing absorbent material extending from one end of the pickup module and adapted to be positioned exterior from the labia-minora area, and fluid-wicking fibers contained in both the pickup and capacity modules. The wicking fibers provide some absorbent capacity and, further, can carry fluid from the pickup module to the capacity module. The present invention includes fluid-wicking fibers provided by longitudinally oriented wicking fibers packed in the capacity module at a bulk density greater than in the pickup module. The interlabial pickup module has a fluid-pervious cover positioned over the absorbent, and the capacity module has a fluid-impervious baffle to contain body fluid therein. In one aspect, the capacity module is adapted to be fit in a position at or near a woman's perineal area. The interlabial sanitary pad can have a flattened, fan-shaped capacity module and can contain a superabsorbent material.

The general object of the present invention is to provide an interlabial sanitary pad to absorb and contain menstrual fluids or other body exudates, including urine. A more specific object of this invention is to provide an interlabial sanitary pad which is comfortable physically and psychologically to the wearer.

Another object of the present invention is to provide an interlabial sanitary pad which is capable of absorbing significant amounts of body fluid.

Still another object of the present invention is to provide an interlabial sanitary pad which is capable of absorbing significant amounts of menses and other body exudates while providing enhanced wearer comfort in feminine care applications.

It is another object of the present invention to provide an interlabial sanitary pad which is capable of absorbing significant amounts of body fluid while providing a low profile of appearance when viewed through a wearer's outer garments.

It is a further object of the present invention to provide an interlabial sanitary pad which is capable of absorbing significant amounts of body fluid while providing enhanced protection against leakage through to a wearer's outer garments.

Other objects and advantages of the present invention will become more apparent to those skilled in the art in view of the following description and the accompanying drawings.

BRIEF DESCRIPTION OF THE DRAWINGS

FIG. 1 is a plan view of an interlabial sanitary pad.

FIG. 2 is a side elevation view of the interlabial sanitary pad shown in FIG. 1.

FIG. 3 is a schematic showing the interlabial sanitary pad as worn on a female body.

FIG. 4 is a perspective view of the interlabial sanitary pad including protective side shields.

FIG. 5 is an end elevation view of the interlabial sanitary pad shown in FIG. 4.

DETAILED DESCRIPTION OF THE PREFERRED EMBODIMENTS

Referring now to FIGS. 1 and 2, an interlabial sanitary pad 10 is shown which includes a pickup module 20 and a capacity module 30.

The pickup module 20 contains loosely fit, fluid absorbent/wicking fibers 22 and is adapted to fit a woman's labia minora area. It is believed that the fluid absorbent/wicking fibers 22 suitable for the present invention can be composed of any absorbent material capable of absorbing and wicking human exudate. Examples of suitable fibers include, but are not limited to, polypropylene fibers, polyester fibers, rayon fibers, cotton fibers, wood pulp fluff fibers, bleached or unbleached, or mixtures of these fibers with or without surfactant treatment.

Preferably, the fluid absorbent/wicking fibers 22 are longitudinally oriented to fit the labia minora area. The fluid absorbent/wicking fibers 22 in the pickup module 20 can be covered by an outer cover 24 pervious to menstrual fluids and other body exudate fluids. A suitable cover material can be a spunbond material.

Inside the cover 24 of the pickup module 20, the fluid absorbent/wicking fibers 22 communicate in fluid flow between the pickup module 20 and the capacity module 30 for carrying fluid from the pickup module 20 to the capacity module 30. The fluid absorbent/wicking fibers 22 preferably are composed of a material capable of wetting and wicking menses or other body exudate fluids. Examples of economical fibers suitable for fluid absorbent/wicking fibers 22 are cellulose acetate tow, e.g., in one embodiment in a tri-lobal cross section, or a rayon tow in a multilobal cross section.

In a preferred embodiment, the fluid absorbent/wicking fibers 22 are loosely packed within the cover of the pickup module 20. The undensified fluid absorbent/wicking fibers 22 in the pickup module 20 are preferably longitudinally oriented and continue into the capacity module 30 where they are packed tighter to form densified wicking fibers 32. This allows for yielding a density gradient between the undensified fluid absorbent/wicking fibers 22 and densified wicking fibers 32 of the different modules 20 and 30, respectively. The longitudinally oriented densified wicking fibers 32 are packed in the capacity module 30 at a bulk density greater than the fluid absorbent/wicking fibers 22 in the pickup module 20. The density gradient promotes the flow of fluid from the pickup module 20 to the capacity module 30.

The capacity module 30 is adapted to be carried on a woman in a position exterior of or remote from contact with the woman's labia minora area. The absorbent material in the capacity module 30 can be any absorbent capable of absorbing human exudate, such as polyester fibers, rayon fibers, cotton fibers, wood pulp fluff fibers, bleached or unbleached, or mixtures of these fibers with or without surfactant treatment.

The capacity module 30 can be constructed to contain a high capacity absorbent or superabsorbent 34 (SAM). The superabsorbent can be one or more materials capable of absorbing many times its own weight of menses or body fluid. The superabsorbent 34 can be provided by such superabsorbent materials as are known to one skilled in the art.

In one aspect, the undensified fluid absorbent/wicking fibers 22 extending from the pickup module 20 into the densified wicking fibers 32 of capacity module 30 can be viewed as a channel communicating between the pickup module 20 and the capacity module 30 for carrying fluid from the pickup module 20 to the capacity module 30. Preferably, the channel contains longitudinally oriented fluid-wicking fibers packed in a differential bulk density which increases from undensified fluid absorbent/wicking fibers 22 to densified wicking fibers 32.

The densified wicking fibers 32 communicate fluid to the high capacity absorbent 34 contained within the capacity module 30. The densified wicking fibers 32 terminate at or near the far end of the capacity module 30 at a position suitable for fluid communication with the high capacity absorbent material 34 which captures and retains the menstrual fluid. The high capacity absorbent material 34 can be superabsorbent as described above.

A fluid-pervious cover 24 surrounds the fluid absorbent/wicking fibers 22 and densified wicking fibers 32. A fluid-impervious baffle 36 surrounds the high capacity absorbent 34 in the capacity module 30.

The capacity module 30 includes the fluid-impervious baffle 36 capable of surrounding the entire capacity module. The fluid-impervious baffle 36 can be a polymer film of polyethylene, polypropylene, or any other material with similar properties including breathable film. The polymer film of the baffle 36 may be combined with a nonwoven material to create a cloth-like outer cover or baffle impervious to fluid. The baffle 36 will block the flow of body fluid onto an outer garment of the body of the wearer.

The capacity module 30 can be configured as a compact structure that expands as it absorbs fluid, or it can be a structure constructed to be at full size initially. The capacity module 30 can have a flattened fan shape to provide comfort to the wearer. In one aspect, the capacity module 30 is adapted to be fit in a position at or near a woman's perineal area.

The higher density fibers 32 draw fluid from the lower density fibers 22 and retain it in capacity module 30. The density of the lower density fibers 22 should be in the range of about 0.03 to about 0.14 g/cm$^3$. A preferred range for the lower density fiber 22, of about 0.07 to about 0.11 g/cm$^3$, provides a desired integrity and bulk. The density of the higher density fibers 32 should be in the range of about 0.14 to about 0.3 g/cm$^3$. A preferred range of the higher density fiber 32, of about 0.16 to about 0.22 g/cm$^3$, provides a desired capillarity without excessive stiffness.

The longitudinally oriented fluid absorbent/wicking fibers can be provided by fibers having a length dimension equal to one-quarter the length of the product to the full length of the product and average or nominal diameters of about 1 micron to 1 mm. The longitudinally oriented densified wicking fibers 32 can have a length dimension equal to one-quarter the length of the product to the full length of the product and average or nominal diameters of about 1 micron to 1 mm.

The pickup module 20 is connected to the capacity module in any of the following manners: Adhesive, heat, ultrasonic bonding, or in any manner that allows for liquid communication between modules.

Without intending to be limited to a specific dimension, the length of the pickup module 20 is indicated as $L_1$ and can be about 50 mm, plus or minus about 5 mm. The width of the pickup module 20 is indicated as $W_1$ and can be about 8 mm, plus or minus about 1 mm. Similarly, the height of the pickup module 20 is indicated as $H_1$ and can be about 15 mm, plus or minus about 2 mm.

Without intending to be limited to a specific dimension, the length of the capacity module 30 is indicated as $L_2$ and can be about 45 mm, plus or minus about 5 mm. The width of the capacity module 30 is indicated as $W_2$ and can be about 35 mm (when full), plus or minus about 4 mm. Similarly, the height of the capacity module 30 is indicated as $H_2$, and can be about 10 mm (when full), plus or minus about 2 mm.

The total absorbance and containment of body fluids in the capacity module 30 is on the order of at least about 12 grams. Such capacity is a significant level of fluid containment compared to prior interlabial sanitary pads.

Referring to FIG. 3, the interlabial sanitary pad 10 is shown applied to a female body. The pickup module 20 is inserted between the labia minora 40. The labia minora 40 is formed by two narrow folds of tissue enclosed within the cleft of the labia majora 50. The labia majora are two rounded folds of tissue that form the external lateral boundaries of the vulva. The length of the pickup module 20 is centered over the vaginal orifice 60. The capacity module 30, as shown in one embodiment, is positioned to the posterior of the labia minora 40 and extends into the perineal area 70. Alternatively, the interlabial sanitary pad 10 can be constructed with the capacity module 30 extending toward the front of the labia minora 40 or with the capacity module 30 extending directly downward from the pickup module 20. The interlabial sanitary pad 10 is held in place by the pressure exerted on it by the labia majora 50 and the surrounding body tissue.

Referring to FIGS. 4 and 5, an interlabial sanitary pad 80 is shown having a pair of protective side shields 82 and 84. The protective side shields 82 and 84 are attached to the posterior of the pickup module 20 to provide protection against fluid leaking onto an outer garment of the wearer.

Accordingly, the present invention provides a feminine personal hygiene care product or sanitary protection device capable of absorbing and containing menstrual fluids, or other natural body exudates, by intercepting menstrual fluid flow with the pickup module 20 located in a position at the labia minora and by wicking the fluid to the capacity module 30 located in a position exterior or outside the labia minora. The feminine sanitary protection device operates to move absorbed fluid to the capacity module 30 at a destination remote from the interlabial positioning of the pickup module 20 and provides for absorption of significant amounts of fluid compared to prior art interlabial sanitary protection devices.

While the invention has been described in conjunction with several embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

We claim:

1. An interlabial sanitary pad comprising:

(a) an absorbent fluid pickup module having a liquid-pervious cover and configured to fit between the labia of a woman, wherein said cover surrounds said pickup module, said pickup module having a first predetermined height dimension; (b) an absorbent fluid capacity module communicating with and extending longitudinally from said pickup module, said capacity module being enclosed in a liquid-impervious baffle, said capacity module having generally a flattened fan shape and adapted to be positioned exterior of said labia, said capacity module having a second predetermined height dimension; and (c) fluid-wicking fibers contained in both said pickup and capacity modules, said fibers are longitudinally oriented and are capable of carrying fluid from said pickup module to said capacity module, said first height dimension of said pickup module being greater than said second height dimension of said capacity module.

2. The interlabial sanitary pad of claim 1 wherein said fluid-wicking fibers comprise longitudinally oriented densified wicking fibers packed in said capacity module at a bulk density greater than undensified fluid absorbent/wicking fibers in said pickup module.

3. The interlabial sanitary pad of claim 1 wherein said capacity module is configured to fit on the wearer in a position rearward from a woman's labia.

4. The interlabial sanitary pad of claim 1 wherein said fluid-wicking fibers are absorbent and can be wetted by menses.

5. The interlabial sanitary pad of claim 4 wherein said capacity module contains superabsorbent particles.

6. The interlabial sanitary pad of claim 5 having a total absorbent capacity of more than about 12 grams.

7. The interlabial sanitary pad of claim 6 having a low profile appearance when viewed through the wearer's outer garments.

8. An interlabial sanitary pad comprising:

(a) a pickup module having a first predetermined height dimension and including a pickup absorbent configured for residing in a woman's vaginal opening and an outer, liquid-pervious cover enclosing said pickup absorbent;

(b) a capacity module having a second predetermined height dimension and containing a capacity absorbent enclosed by a liquid-impervious baffle, said capacity module structured to be positioned exterior of said vaginal opening and having generally a flattened fan shape; and (c) fluid flow means for carrying fluid from said pickup module to said capacity module, said fluid flow means including longitudinally oriented fluid-wicking fibers packed in said capacity module at a bulk density greater than in said pickup module, said fibers having a length of at least one quarter of said interlabial pad, said pickup module having a height dimension at least 50% greater than said capacity module.

9. The interlabial sanitary pad of claim 8 wherein said capacity module is structured to be positioned rearward from the wearer's labia.

10. The interlabial sanitary pad of claim 8 wherein said capacity module is structured to be positioned on the wearer at an angle downward and exterior from contact with the wearer's labia.

11. The interlabial sanitary pad of claim 10 wherein said fluid-wicking fibers comprise said pickup absorbent, further comprise said capacity absorbent, and can be wetted by menses.

12. The interlabial sanitary pad of claim 11 wherein said capacity module contains superabsorbent particles.

13. The interlabial sanitary pad of claim 11 having a total absorbent capacity of more than about 12 grams.

14. The interlabial sanitary pad of claim 13 having a low profile appearance when viewed through the outer garments of a wearer.

15. A method for making a feminine care sanitary protection device comprising:

(a) providing a pickup module having an outer, liquid pervious cover and an absorbent portion suitable for residing in a woman's labial area;

(b) providing a capacity module containing absorbent and a liquid-impervious baffle, the capacity module adapted to reside in a wearer's perineal area in a flattened fan shape; and (c) establishing fluid-wicking fibers communicating with the pickup and capacity modules for carrying fluid from the pickup module to the capacity module, wherein said fluid-wicking fibers comprise longitudinally oriented wicking fibers packed in said capacity module in a bulk density greater than in said pickup module.

16. An interlabial sanitary pad having a low profile appearance when viewed through the wearer's outer garments comprising:

(a) a pickup module including a pickup absorbent configured for positioning at a woman's vaginal opening and an outer, liquid-pervious cover enclosing said pickup absorbent;

(b) a capacity module extending longitudinally from said pickup module and containing a capacity absorbent enclosed by a liquid-impervious baffle and configured for residing in a wearer's perineal area remote from contact with said vaginal opening, said capacity module having a generally flattened fan shape and a pair of protective wings for protecting adjacent clothing from being stained by body fluid;

(c) fluid-wicking fibers communicating with both said pickup and capacity modules for absorbing fluid and for carrying fluid from said pickup module to said capacity module, said fluid-wicking fibers comprising longitudinally oriented fibers packed in said pickup module at a bulk density in the range of about 0.07–0.11 $g/cm^3$ and longitudinally oriented fibers packed in said capacity module at a bulk density of about 0.16–0.22 $g/cm^3$; and (d) superabsorbent positioned within said capacity module for absorbing and containing menses and other body fluids, said capacity module having a total absorbent capacity greater than about 12 grams.

\* \* \* \* \*